United States Patent [19]

Dawes et al.

[11] 4,196,096
[45] Apr. 1, 1980

[54] PROCESS FOR REGENERATION OF RHODIUM HYDROFORMYLATION CATALYSTS

[75] Inventors: John L. Dawes; Thomas J. Devon, both of Longview, Tex.

[73] Assignee: Eastman Kodak Company, Rochester, N.Y.

[21] Appl. No.: 11,604

[22] Filed: Feb. 12, 1979

[51] Int. Cl.$^2$ ............................................. B01J 27/28
[52] U.S. Cl. .................................................. 252/414
[58] Field of Search ......................................... 252/414

[56] References Cited

U.S. PATENT DOCUMENTS

| | | | |
|---|---|---|---|
| 2,794,039 | 5/1957 | Lake | 252/414 X |
| 4,135,911 | 1/1979 | Balmar | 252/414 X |

FOREIGN PATENT DOCUMENTS 2311388  9/1974  Fed. Rep. of Germany ........... 252/414

Primary Examiner—Patrick Garvin
Attorney, Agent, or Firm—Edward R. Weber; Daniel B. Reece, III

[57] ABSTRACT

Rhodium hydroformylation catalysts are regenerated by a novel process which includes the steps of removing the catalyst to be regenerated from the hydroformylation reaction, adjusting the aldehyde contents of the catalyst containing stream so as to have at least one mole of aldehyde present per mole of rhodium and ligand present in the catalyst, treating the aldehyde containing catalyst stream with oxygen or oxygen containing gas at a temperature less than the boiling point of the aldehyde, removing any solid material formed during the oxidation and adjusting the ligand to rhodium ratio as required for use in the hydroformylation reaction.

12 Claims, No Drawings

PROCESS FOR REGENERATION OF RHODIUM HYDROFORMYLATION CATALYSTS

This invention relates to the oxo process for the hydroformylation of olefins or other unsaturated compounds by the reaction of the unsaturated compound with carbon monoxide and hydrogen in the presence of a catalyst. More specifically, this reaction relates to a method of regenerating a rhodium complex catalyst useful in such a hydroformylation reaction. Oxo reactions are normally carried out in the presence of cobalt metal based catalysts. This type of catalysis is commercially efficient even though it produces a significant quantity of by-products such as paraffins, alcohols, acetals, aldol type products and other high boilers. By contrast, rhodium based catalysis gives greatly increased selectivity to the desired product often as high as 99 percent. Rhodium based catalysts are also functional at much lower temperatures and pressures. This results in significantly lower equipment and utilities requirements needed to build and operate a rhodium catalyst oxo facility. Typical rhodium complex catalysts used in hydroformylation reaction consist of rhodium metal in combination with a ligand or functional group that activates rhodium into a hydroformylation catalyst under reaction conditions.

There are many known ligands which can modify rhodium products to produce complex catalysts useful in oxo reactions. Several rhodium complexes which may typically be reactivated by the process of the instant invention contain ligands such as triaryl, trialkyl or mixed aryl alkyl amines, phosphines, arsines or stilbines. These complexes are generally referred to as oxo catalysts. When placed in an oxo reaction they become even more complex by reacting with the hydrogen and carbon monoxide that is present. Rhodium with triphenylphosphine ligands, for example, becomes a complex of rhodium hydride, carbonyl and triphenylphosphine.

During hydroformylation reactions, rhodium oxo catalysts deactivate to a point where they have insufficient activity to support economical reactivity. Normally a fully active rhodium oxo catalyst complex is straw colored while an inactive complex is black. Monitoring this color change is one practical method of determining if a catalyst is active or inactive. The chemical structure of an inactive catalyst complex is unknown. It is presumed to be rhodium cluster compounds containing carbon monoxide and possibly other ligands.

A principal disadvantage of a rhodium catalyzed oxo process is the extremely high capital investment needed for the initial catalyst charge (rhodium cost is in excess of $5,000 per pound) along with the lack of an effective method for catalyst reactivation without significant loss in the valuable rhodium component. At least three methods of regeneration have been suggested in the prior art. U.S. Pat. No. 3,555,098 describes the use of water or caustic as a wash for the catalyst. This method removes such poisons as acids but has not been effective for regeneration of dead cluster rhodium compounds. Japanese Pat. No. 73/43799 describes reduction using hydrogen as a suitable regeneration method. Japanese Patent No. 74/94385 describes the use of molecular oxygen for regeneration in the absence of aldehydes. None of the aforementioned methods are successful in restoring virtually fresh catalyst activity without significant loss of rhodium.

In an attempt to discover suitable regeneration procedures, numerous procedures have been tested. These included treating the dead catalyst with hydrogen, carbon monoxide, synthesis gas (the combination of carbon monoxide and hydrogen used in the oxo reaction); washing the dead catalyst with water or aqueous caustic; refluxing the dead catalysts with aqueous caustic or an acetic acid anhydride mixture; treating the dead catalyst with hydrochloric acid followed by a sodium isobutyrate wash; treating the dead catalyst with reducing agents, e.g., sodium borohydride in methanol or hydrazine in ethanol; and treating the catalyst with air in the absence of aldehyde. None of these procedures proved adequate for use as a catalyst regeneration method.

The method of the instant invention consists of removing all or a portion of an inactive catalyst from a hydroformylation reaction, adjusting the aldehyde content so as to have at least one mole of aldehyde present for each mole of rhodium and ligand present, treating the aldehyde containing catalyst with oxygen or an oxygen containing gas at a temperature not exceeding the boiling point of the aldehyde, removing any solid material formed during the oxidation and adding replacement ligand to bring the rhodium/ligand ratio into the desired molecular balance. Optionally, it may be desirable to remove excess ligand from the catalyst prior to the adjustment of aldehydes; this will serve to reduce the amount of ligand lost by oxidation and also reduce the amount of aldehyde which must be added to achieve the correct aldehyde/rhodium/ligand balance. In addition, following oxidation, it may be desirable to treat the catalyst so as to remove any acid produced during the oxidation step.

The exact mechanism of reactivation is not fully understood, however, it is believed to involve the formation of peroxy species through the reaction of oxygen and aldehyde. These peroxy species apparently oxidize the ligands present and thus facilitate the breakup of the rhodium clusters. The rhodium clusters, broken up during the regeneration, are believed to go to a mono or dimeric rhodium carboxylated complexes. The ligands oxidized by the peroxy species, e.g., the phosphines and amines, are converted to the corresponding oxides, e.g., phosphine oxides or amine oxides. Once the ligands are oxidized their ligand power is reduced and the rhodium clusters can be attacked by the peroxy species, oxidized and broken up to form, for example, rhodium dicarboxylate complexes. This method has been found to result in a virtually complete reactivation of catalyst with minimal rhodium loss and may be used repeatedly on the same catalyst charge without the build-up of undesirable by-products. Surprisingly it has been found that this method is also effective in reactivating rhodium oxo catalysts which have been poisoned by sulfur.

Because of the mild conditions required, the process may be carried out at atmospheric conditions in inexpensive equipment. In addition to the oxidation step which constitutes the heart of the instant invention, at least one other parameter in the process is considered essential. Aldehyde in a slight molar excess must be present prior to the oxidation step. Typically, a mole of rhodium and a mole of ligand would require the presence of about 2.05 moles of aldehyde. The aldehyde used would preferably be one inherent to the aldehydes being produced, such as iso or normal butyraldehyde, propionaldehyde, 2-ethylhexaldehyde or a low boiling aldehyde such as acetaldehyde. Because of this requirement for a slight excess of aldehyde, it is obvious that it may be desirable to remove any excess free ligand prior to the aldehyde adjustment and oxidation step. In order to prevent the build-up of acids in the catalyst stream it may also be desirable that the acid formed in the oxidation step be removed from the reactivated catalyst prior to its reuse.

In a more specific illustration of an embodiment of the instant invention a rhodium catalyst utilized in a process such as that described in U.S. Pat. No. 3,527,809 can be removed as a slip stream from the process. For each mole of rhodium and ligand present in the slip stream an equal molar amount of aldehyde plus a slight excess of aldehyde is added. The aldehydes are preferably iso- or normal butyraldehydes or mixtures thereof. Air is then blown through the solution at a slow rate so the temperature of the mixture does not rise rapidly. As reactivation proceeds the solution goes from a black color to a straw color. Typically this will take from a few minutes (30 or less) to 48 hours or more. Excess aldehyde and any acids formed during oxidation are then removed. The amount of aldehyde and air used in the oxidation are controlled to minimize the formation of acid in the regeneration process. The solution is then filtered to remove any solids, for example triphenylphosphine oxide, and returned to the catalyst recycle stream with added phosphine. Progress of this air-aldehyde catalyst regeneration can be monitored by the change in color from the dark deactivated form to the straw yellow of the active form. Regeneration is not complete until all the phosphine, etc., is oxidized to the phosphine oxide. When excess phosphine is employed in the reaction it should be removed from the stream prior to regeneration by methods known in the art and then replaced after the regeneration.

The following exemplary descriptions will illustrate more fully the functioning of the instant invention, but it should be understood that they are not to be construed as limiting the invention in any manner. (In the following examples triphenylphosphine is represented by the symbol $P\phi_3$.)

EXAMPLE 1

This example shows that deactivated catalyst has only 22 percent the activity of a standard fresh catalyst. A sample of $HRh(CO)(P\phi_3)_3 + 16\ P\phi_3$ oxo catalyst, deactivated in propylene hydroformylation at 100° C. and 1,000 psig, is removed from the reactor, stripped in vacuo and divided into four portions. The first portion is diluted with isobutyraldehyde to 55 ppm rhodium and tested for propylene hydroformylation at 100° C. and 1,000 psig. Butyraldehydes are produced at a rate of 11 pounds per cubic foot per hour.

EXAMPLE 2

This example shows that addition of 19 g moles $P\phi_3$ per g atom Rh does not enhance the activity of the deactivated catalyst (and shows that loss of $P\phi_3$ is not the cause of deactivation).

The second portion from Example 1 is diluted with isobutyraldehyde to 55 ppm rhodium, 19 g moles of $P\phi_3$ are added per g atom of rhodium and tested for propylene hydroformylation at 100° C. and 1,000 psig. Butyraldehyde is produced at the same rate as Example 1 above.

EXAMPLE 3

This example shows that oxidized catalyst without added phosphine is only 27 percent as active as fresh catalyst. The two portions remaining from Example 1 are combined, diluted with isobutyraldehyde and treated at room temperature with a slow stream of air for 48 hours. The solution lightens from black to a straw yellow and all the triphenylphosphine is oxidized to triphenylphosphine oxide. The solvent is stripped in vacuo at 100° C. to remove the isobutyric acid produced in the oxidation. The residue is diluted with isobutyraldehyde to 55 ppm rhodium and divided into two parts. The first part is tested for propylene hydroformylation at 100° C. and 1,000 psig and produces butyraldehydes at a rate of 14 pounds per cubic foot per hour.

EXAMPLE 4

This example shows that oxidized catalyst with 19 moles of phosphine is as active as fresh catalyst. The second portion from Example 3 is treated with 19 equivalents of triphenylphosphine per equivalent of rhodium and tested in a similar manner. It produces butyraldehydes at 51 pounds per cubic foot per hour equivalent to a fresh $HRh(CO)(P\phi_3)_3 + 16\ P\phi_3$ catalyst under identical conditions.

EXAMPLE 5

This example shows that isobutyric acid and air will not regenerate the catalyst in the absence of aldehyde. A sample of deactivated rhodium oxo catalyst is stripped of all aldehyde, diluted with 100 ml isobutyric acid and treated with air for 5 days at room temperature. The solution remains black. After stripping, addition of 19 moles triphenylphosphine and dilution to 55 ppm rhodium with isobutyraldehyde, the propylene hydroformylation activity is the same as it was before the attempted regeneration.

EXAMPLE 6

This example shows that a combination of isobutyric acid and hydrogen peroxide partially regenerates the deactivated catalyst but is not as effective as the air-/aldehyde regeneration. A sample of deactivated catalyst is stripped to remove all aldehydes. It is diluted to 100 ml with isobutyric acid and treated with a 300 percent excess of hydrogen peroxide at room temperature for 2 hours. After stripping, adding 19 equivalents of triphenylphosphine and testing in isobutyraldehyde, the activity is 85 percent of that of a fresh catalyst.

EXAMPLE 7

Oxidation was continued for 3 days under conditions as set forth in Example 6 but still gave a catalyst only 85 percent as active as fresh catalyst.

EXAMPLES 8-16

These examples show the use of electron transfer agents in attempted regenerations of deactivated rhodium complex catalysts. The method by which the regeneration is attempted is as follows:

A 100 ml aliquot of deactivated rhodium oxo catalyst which contains $\phi_3P$ to Rh in a 19 to 1 mole ratio is stripped of aldehyde to leave a dark rhodium bearing residue of condensation products. Isobutyric acid (5 ml) and 2,3-dichloro-5,6-dicyanobenzoquinone (0.25 gram) are added to the residue and the mixture heated to 130° for 15 minutes. After this period, the isobutyric acid and half of the high boilers are removed by gas stripping. Triphenylphosphine (1.9 grams), equivalent to a 19 molar excess of the amount of rhodium in the residue is added. Isobutyraldehyde (700 ml) is added to make up a catalyst solution containing 55 ppm Rh. The solution is evaluated for catalytic activity by running under 1,000 psig synthesis gas at 100° with propylene.

The results of these attempted regenerations are shown in Table I.

TABLE I

| Example Number | Inactive Catalyst Treated With | % Activity of Fresh Catalyst |
|---|---|---|
| 8 | 0.24 Grams of 2,5-di-t-Butyl-benzoquinone in Isobutyric Acid at 130° for 15 Minutes | 0 |
| 9 | 0.25 Grams of Dichloro-dicyanobenzoquinone (DDQ) in Isobutyric Acid at 130° for 15 Minutes | 0 |
| 10 | 0.61 Grams of $(NH_4)_2Ce(NO_3)_6$ in Acetic Acid at 105° for 30 Minutes | 4.9 |
| 11 | 0.35 Grams of Ferric Isobutyrate in Isobutyric Acid at 130° for 15 Minutes | 0 |
| 12 | 0.35 Grams of Ferric Isobutyrate in Trifluoroacetic Acid at 100° for 2 Hours | 20 |
| 13 | Trifluoro Acetic Acid at 100° for 2 Hours | 0 |
| 14 | 0.72 Grams Ceric Trifluoroacetate in Trifluoroacetic Acid at 100° for 2 Hours | 7.3 |
| 15 | 0.13 Grams of DDQ in Trifluoroacetic Acid at 100° for 2 Hours | 0 |
| 16 | 0.44 Grams of $Cu(OAc)_2.H_2O$ in $HOAc/H_2O$ at Reflux for 15 Hours | 29 |

EXAMPLE 17

This example shows an incomplete regeneration via electrolysis of an inactive rhodium oxo catalyst. The dark high boiling residues from inactive rhodium oxo catalyst are charged into 250 ml electrochemical cell which is equipped with a nitrogen purge and two concentric platinum screen electrodes. Sodium isobutyrate (1.0 gram) and 200 ml of absolute ethanol are added to the cell and stirred. Voltage is applied to the mixture for 41 hours. The color of the initially dark solution has faded to a dark honey color at the end of electrolysis. Triphenylphosphine (1.9 grams) is added to the mixture. The ethanol is removed by stripping. The residue is taken up in toluene and washed with water to remove the sodium isobutyrate. The catalyst solution is made up by adding isobutyraldehyde to the toluene extract. The solution is evaluated for catalytic activity by reacting with propylene at 100° at 1,000 psig of synthesis gas. The activity is 60 percent of a fresh catalyst.

The following examples show that partial, but not complete regeneration is obtained by exposure of deactivated rhodium oxo catalyst to air at elevated temperatures in the absence of aldehyde.

EXAMPLE 18

The following procedure is utilized for carrying out an oxo run with rhodium oxo catalyst.

Triphenylphosphine (0.228 g, 0.869 m mole), $RhH(CO)(\phi_3P)_3$ (0.050 g, 0.054 m mole) and 91 ml of distilled Texanol™ ester-alcohol are charged into a 300 ml Hastelloy-C Autoclave Engineers Magnedrive autoclave under a nitrogen blanket. After torquing the head, the system is purged with nitrogen. The autoclave is valved off and chilled in a dry ice-acetone bath. A tared bomb containing a known weight of propylene (21 g) is connected to the vent of the autoclave. The propylene is allowed to condense into the cold autoclave for five minutes before the autoclave is valved off and the bomb removed. The system is warmed to room temperature and pressured to 1,000 psig with synthesis gas. The reaction is carried out at 100° for 30 minutes. The system is pressured with synthesis gas to 1,000 psig pressure whenever the pressure drops to 900 psig. A total pressure drop of 950 pounds is observed. The autoclave is valved off and removed from the cubical after being cooled to 30°. After removal from the cubical, the autoclave is chilled in an ice water slush prior to slow venting. The liquid products are removed and chromatographed. The weights of n- and isobutyraldehyde products are determined using chromatography factors with the Texanol ester-alcohol solvent as an internal standard. The total weight of butyraldehyde product is 15.2 g with an n/iso ratio of 1.76.

EXAMPLE 19

This example shows that partial recovery of oxo activity is obtained from the exposure of deactivated rhodium oxo catalyst to air in the absence of aldehyde at 130° for 15 minutes. The synthesis gas batch is the same as Example 18.

A 34 ml aliquot (0.054 m moles Rh) of inactive rhodium oxo pilot plant catalyst is transferred under nitrogen to a round bottomed flask. A rotary evaporator with a greased ground glass joint is used to strip the contents of the round bottomed flask. Butyraldehyde and other low and intermediate boiling compounds are removed by stripping down to 4 mm Hg° at 135° for two hours to remove the bulk of the solvent. At the end of this time, the system is allowed to return to atmospheric pressure using air. The flask is rotating and is maintained at 135°. The conditions are maintained for 15 minutes, during which the residues noticeably lightened in color. The flask is cooled and the residue (net weight 2.9 g) analyzed by thin layer chromatography for triphenylphosphine. No triphenylphosphine is detected. Make-up triphenylphosphine (0.271 g, 1.034 m mole) is added to the residue along with 91 ml of distilled Texanol ester-alcohol. The light brown solution is charged into the 300 ml autoclave described in Example 18 under a nitrogen blanket. Propylene (20 g) is charged into the autoclave in the manner described in Example 19. The system is evaluated for catalytic activity using the same procedure as Example 19. The run has a pressure drop of 630 pounds and produces 10.37 g of butyraldehyde, having a normal/iso ratio of 1.78.

The activity is 68% of a fresh catalyst.

EXAMPLE 21

When the deactivated catalyst is exposed to air in the absence of aldehyde at 135° for 1 minute the activity is 60% of the fresh catalyst. (Other conditions are the same as Example 19.)

The unregenerated deactivated catalyst has 22% the activity of a fresh catalyst.

The invention has been described in detail with particular reference to certain preferred embodiments thereof, but it will be understood that variations and modifications can be effected within the spirit and scope of the invention.

We claim:

1. A method of regenerating a rhodium hydroformylation catalyst which includes:
   (a) adjusting the aldehyde content of the catalyst to be regenerated so as to have at least one mole of aldehyde present per mole of rhodium and ligand present in the catalyst,
   (b) treating the aldehyde-containing catalyst with an oxygen-containing gas at a temperature less than the boiling point of the aldehyde,
   (c) removing any solid material formed during the oxidation, and
   (d) adjusting the ligand to rhodium ratio of the regenerated catalyst as required for use in the hydroformylation reaction.

2. A process according to claim 1 wherein the oxygen-containing gas is air.

3. A process according to claim 1 wherein the regeneration is continued until the catalyst has changed from a dark brownish-black color to a light straw color.

4. A process according to claim 1 wherein uncombined ligand is removed from the catalyst prior to the adjustment of the aldehyde to rhodium/ligand ratio.

5. A process of claim 1 wherein aldehyde is present to the extent of at least 1.025 moles per mole of rhodium and ligand present in the catalyst being regenerated.

6. A process of claim 1 wherein any acid produced during the regeneration is removed from the regenerated catalyst prior to the adjustment of the rhodium ligand ratio for reintroduction into the hydroformylation reaction.

7. A method for regenerating a rhodium hydroformylation catalyst which includes;
   (a) removing a portion of a catalyst which has become at least partially inactive from a hydroformylation reactor,
   (b) adjusting the aldehyde content so as to have at least one mole of aldehyde present per mole of rhodium and ligand present in the catalyst,
   (c) treating the aldehyde-containing catalyst with an oxygen-containing gas at a temperature less than the boiling point of the aldehyde,
   (d) filtering the regenerated catalyst to remove any solid material formed during the oxidation.

8. A process according to claim 7 wherein the oxygen-containing gas is air.

9. A process according to claim 7 wherein the regeneration is continued until the catalyst has changed from a dark brownish-black color to a light straw color.

10. A process according to claim 7 wherein uncombined ligand is removed from the catalyst prior to the adjustment of the aldehyde to rhodium/ligand ratio.

11. A process of claim 7 wherein aldehyde is present to the extent of at least 1.025 moles per mole of rhodium and ligand present in the catalyst being regenerated.

12. A process of claim 7 wherein any acid produced during the regeneration is removed from the regenerated catalyst prior to the adjustment of the rhodium ligand ratio for reintroduction into the hydroformylation reaction.

* * * * *